United States Patent [19]

Boden et al.

[11] Patent Number: 5,360,911
[45] Date of Patent: Nov. 1, 1994

[54] PROCESS FOR THE PREPARATION OF STILBAZOLIUM SALTS

[75] Inventors: Eugene P. Boden, Scotia; Peter D. Phelps; Kevin R. Stewart, both of Schenectady, all of N.Y.

[73] Assignee: General Electric Company, Schenectady, N.Y.

[21] Appl. No.: 77,263

[22] Filed: Jun. 17, 1993

[51] Int. Cl.⁵ ............................................. C07D 213/18
[52] U.S. Cl. ...................................... 546/347; 546/348; 546/349; 546/352
[58] Field of Search ................ 546/347, 348, 349, 352

[56] References Cited

U.S. PATENT DOCUMENTS 3,085,935  4/1963  Phillips et al. ...................... 546/347

OTHER PUBLICATIONS

J. Org. Chemistry, 49, 2546–51, 1984.

Primary Examiner—Robert T. Bond
Assistant Examiner—Y. N. Gupta
Attorney, Agent, or Firm—William H. Pittman

[57] ABSTRACT

A novel process is disclosed for producing stilbazolium salts. Said novel process employs a heterocyclic amine catalyst, such as pyrrolidine, an alkylated pyridine salt and a substituted benzaldehyde which unexpectedly results in increased reaction rates and product yields.

19 Claims, No Drawings

PROCESS FOR THE PREPARATION OF STILBAZOLIUM SALTS

The following invention was made with government support via contract number F4962091-C-0075 which was awarded by the United States Air Force. The government has certain rights in this invention.

FIELD OF THE INVENTION

This invention relates to a novel process for producing stilbazolium salts. Said novel process utilizes a heterocyclic amine as the preferred catalyst which unexpectedly results in increased reaction rates and product yields.

BACKGROUND OF THE INVENTION

The optics and electronics industries rely upon inorganic compounds for fabrication of various components. However, these industries have frequently ignored the many benefits that may be obtained when employing organic compounds. It has been recently recognized that organic compounds with delocalized pi-electron systems may exhibit large nonlinear optical responses. In many cases, the responses are larger and more favorable than those displayed by inorganic counterparts.

Of the many potential applications of organic compounds to the industries mentioned above, many relate to the electro-optic effect as described by Kerr (1875) and Pockels (1906). Additionally, frequency doubling by second harmonic generation (SHG) is often considered. SHG may be defined as the doubling of lights fundamental frequency.

A test to study SHG has been developed (Kurtz and Perry, 1968) which analyzes, for instance, the noncentrosymmetric crystal structure of organic compounds. Organic compounds which possess a noncentrosymmetric structure exhibit optical nonlinearity and are generally said to be nonlinear.

Organic nonlinear chemical compounds displaying high SHG properties are potentially useful in applications which require high speed optical modulators. Such applications include high speed long distance data links and electric field sensors for use in electromagnetically noisy environments. In addition, such materials provide efficient wavelength shifting capability for optical and infrared remote sensing (e.g., of pollutant particulate concentration) and diode laser frequency doubling for optical data storage.

The known processes for producing nonlinear organic chemical compounds, such as stilbazolium salts, require piperidine (often in excess amounts) as a catalyst. Piperidine is the catalyst of choice because it generally produces acceptable reaction rates in alkylation reactions. Use of piperidine to produce the nonlinear organic chemical compounds described herein is a major obstacle. This is true because piperidine is a highly controlled and regulated chemical substance since it is a well known precursor for phencyclidine (PCP).

The present invention, therefore, is based on the discovery of a process for producing stilbazolium salts without requiring piperidine as a catalyst. An additional embodiment of the instant invention is the use of a heterocyclic amine catalyst that unexpectedly results in increased reaction rates and product yields. In the instant invention, the stilbazolium salts produced are substantially pure wherein substantially pure is defined as at least about 95% pure.

DESCRIPTION OF THE PRIOR ART

Accordingly, processes for producing stilbazolium salts are known in the art. In Marder et al., Science 245, 626–628 (1989) a process for preparing stilbazolium salts is described. In said process, excess amounts of piperidine are utilized; as a result of this, recrystallization steps are required in order to obtain a substantially pure product.

In commonly assigned U.S. Pat. Nos. 5,094,553 and 5,194,984, optical devices comprising stilbazolium salts are disclosed. In said patents, the production of stilbazolium salts is mentioned and piperidine is the required catalyst.

Other investigators have focused on the production of deuterated organic salts. In commonly assigned copending application, Ser. No. 08/067,929, deuterated organic salts are prepared by a process employing piperidine as a catalyst.

The instant process is patentably distinguishable from the processes described above, since among other reasons, it does not require piperidine as an amine catalyst. Furthermore, the instant process employs heterocyclic amine catalysts that unexpectedly result in reaction rates and product yields far greater than rates and yields observed when conventional catalysts, such as piperidine, are employed.

SUMMARY OF THE INVENTION

The present invention therefore is based on the discovery of a process for producing stilbazolium salts without requiring piperidine as a catalyst. More particularly, said process employs a heterocyclic amine catalyst represented by the formula

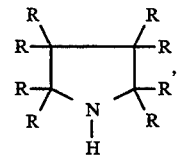

wherein each R is independently a hydrogen, aliphatic, alicyclic or aromatic radical. However, it is preferred that the heterocyclic amine catalyst is pyrrolidine and represented by the formula

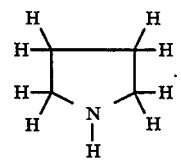

Additionally, the heterocyclic amine catalyst employed in the instant invention may include a mixture of I and II.

DETAILED DESCRIPTION OF THE PREFERRED EMBODIMENTS

The present invention provides for a more efficient method of producing substantially pure nonlinear organic chemical compounds such as stilbazolium salts. The stilbazolium salts that may be prepared via the instant invention include but are not limited to 4′-dimethylamino-N-methylstilbazolium p-toluenesulfonate, 4'-dimethylamino-N-methylstilbazolium methanesulfonate and 4'-methoxy-N-methylstilbazolium p-toluenesulfonate.

The stilbazolium salts prepared by the instant invention are useful in the fabrication of optical materials. The light transmitting properties of said compounds are based on their different crystalline structures and degrees of hydration thereof. Moreover, electro-optic modulators may be prepared from the compounds produced via the instant invention since they possess light transmitting properties which can be varied by application of an electric field.

Additionally, optical waveguides, such as those described in U.S. Pat. Nos. 5,094,553 and 5,194,984, may be prepared from the substantially pure nonlinear organic chemical compounds prepared by the instant invention since they possess light transmitting properties resulting from different crystalline structures.

The novel process for producing the stilbazolium salts of the instant invention is achieved by combining an alkylated pyridine salt with a substituted benzaldehyde in the presence of the heterocyclic amine catalyst previously described.

Said novel process may be further described via the reaction conditions which follow.

An alkylated pyridine salt (such as a picoline salt prepared from 4-picoline and an organic sulfonate ester) and a substituted benzaldehyde (such as dimethylaminobenzaldehyde or p-methoxybenzaldehyde) are combined to produce a salt stock solution. Said salt stock solution may comprise a solvent such as an aliphatic alcohol. Examples of said aliphatic alcohol include methanol, ethanol or propanol. The salt stock solution is heated in a reaction vessel, and subsequently a heterocyclic amine catalyst is added in order to induce formation of the desired stilbazolium salts. Said stilbazolium salts may be recovered via conventional filtration techniques.

The heterocyclic amine catalysts referred to above include all heterocyclic amine catalysts including such amines as piperidine and morpholine. However, new and unexpected results are obtained in the form of increased reaction rates and product yields when the heterocyclic amine catalysts are represented by formula I, formula II or mixtures thereof. It should be noted that the reactants above may also be deuterated or perdeuterated in order to produce a deuterium containing stilbazolium salt.

The following examples and table are provided to further facilitate the understanding of the invention, and they are not intended to limit the instant invention. Additionally, all stilbazolium salts produced can be confirmed by conventional techniques such as proton and carbon 13 nuclear magnetic resonance spectroscopy as well as x-ray crystallographic techniques.

EXAMPLE 1

A dry 500 mL flask was charged with 87.45 grams of methyl toluenesulfonate and 377 ml of methanol under an argon atmosphere to produce a solution. 45.80 grams of 4-picoline were added to the resulting solution to produce a second solution which was warmed (about 75° C.) overnight. The product was a picoline salt solution containing 0.304 grams of alkylated picoline salt/gram of solution (0.912 g/mL). (Additional alkylated pyridine salt solutions may be prepared by employing other organic sulfonate esters such as methyl toluenesulfonate.)

EXAMPLE 2

A 250 mL flask was charged with 7.50 grams (0.05 moles) of dimethylaminobenzaldehyde and 50 mL (0.049 moles) of picoline salt solution (as prepared in Example 1) to produce a salt stock solution. 0.10 equivalents of pyrrolidine were added to the salt stock solution to produce a reaction mixture. Said reaction mixture was refluxed overnight and a substantially pure 4'-dimethylamino-N-methylstilbazolium p-toluenesulfonate precipitate formed. The substantially pure precipitate was recovered by filtration (18.3 grams, 90.0% yield).

EXAMPLE 3

A process similar to the one described in Example 2 was carried out with 0.25 equivalents pyrrolidine. The resulting reaction mixture was refluxed for 2 hours. 18.2 grams (90.0% yield) of substantially pure 4'-dimethylamino-N-methylstilbazolium p-toluenesulfonate precipitated and was recovered via filtration.

EXAMPLE 4

A 500 ml flask was charged with 30.0 grams (0.22 moles) p-methoxybenzaldehyde, 704.5 ml (0.69 moles) of picoline salt solution (as prepared in Example 1) and 0.25 equivalents of pyrrolidine to produce a reaction mixture. Said reaction mixture was refluxed for 3 hours to produce a noncrystalline salt solution. 500 mL of ether were added (since the salt produced is extremely soluble in methanol) and 82.38 grams(97.0% yield) of substantially pure 4-methoxy-N-methylstilbazolium p-toluenesulfonate crystals were recovered by filtration.

The data in the table which follows has been compiled to confirm the new and unexpected results obtained as a result of utilizing the heterocyclic amine catalysts described in the instant invention. All entries have been prepared in the manner described by Examples 1 and 2.

| Entry | Catalyst | Concentration* | Initial Product Formation | Final Product Formation | % Yield |
|---|---|---|---|---|---|
| 1 | Piperidine | 0.25 | 3 hours | 12 hours | 84 |
| 2 | Pyrrolidine | 0.25 | 20 minutes | 1.5 hours | 94 |
| 3 | Diethylamine | 0.25 | — | 12 hours | 43 |
| 4 | Morpholine | 0.25 | 4 hours | 12 hours | 80 |

*Units are equivalents.

Furthermore, when about stoichiometric amounts of starting materials as well as low levels of catalyst (about 0.10 to about 0.25 equivalents per mole of substituted benzaldehyde) and solvent (about 1.0 M) are utilized, the desired stilbazolium salts form and saturate the solvent solution quickly. Hence, a greater yield of substantially pure crystalline product is obtained at increased reaction rates.

Moreover, about 0.05 equivalents of catalyst were sufficient to slowly catalyze the reaction when employing pyrrolidine. A range of about 0.10 to about 0.15 equivalents was an ample amount of catalyst to complete the reactions within several hours when pyrrolidine was utilized.

What is claimed is:

1. A process for producing a stilbazolium salt by combining an alkylated pyridine salt with a substituted benzaldehyde in the presence of about 0.10 to about 0.25 equivalents of a heterocyclic amine catalyst of the formula

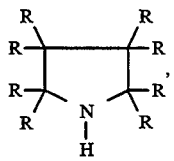

wherein each R is independently a hydrogen, aliphatic, alicyclic or aromatic radical.

2. A process for producing a stilbazolium salt comprising the steps of:
   (a) combining an alkylated pyridine salt and a substituted benzaldehyde to produce a salt stock solution;
   (b) adding to said salt stock solution about 0.10 to about 0.25 equivalents of a heterocyclic amine catalyst of the formula

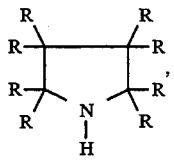

wherein each R is independently a hydrogen, aliphatic, alicyclic or aromatic radical;
   (c) allowing said stilbazolium salt to precipitate;
   (d) recovering said stilbazolium salt in substantially pure form.

3. A process in accordance with claim 2 wherein said heterocyclic amine catalyst is represented by the formula

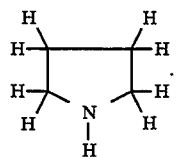

4. A process in accordance with claim 2 wherein said stilbazolium salt is 4'-dimethylamino-N-methylstilbazolium p-toluenesulfonate.

5. A process in accordance with claim 2 wherein said stilbazolium salt is 4-dimethylamino-N-methylstilbazolium methanesulfonate.

6. A process in accordance with claim 2 wherein said stilbazolium salt is 4-methoxy-N-methylstilbazolium p-toluenesulfonate.

7. A process in accordance with claim 2 wherein said alkylated pyridine salt is a picoline salt.

8. A process in accordance with claim 7 wherein said picoline salt is prepared from 4-picoline and an organic sulfonate ester.

9. A process in accordance with claim 8 wherein said organic sulfonate ester is methanesulfonate or methyl p-toluenesulfonate.

10. A process in accordance with claim 2 wherein said salt stock solution comprises a solvent.

11. A process in accordance with claim 10 wherein said solvent is an aliphatic alcohol.

12. A process in accordance with claim 11 wherein said aliphatic alcohol is methanol, ethanol or propanol.

13. A process in accordance with claim 2 wherein said substituted benzaldehyde is dimethylaminobenzaldehyde or p-methoxybenzaldehyde.

14. A process in accordance with claim 2 wherein about 0.10 to about 0.15 equivalents of heterocyclic amine catalyst is added to said salt stock solution.

15. A process in accordance with claim 2 wherein said stilbazolium salt is recovered by filtration.

16. A process in accordance with claim 1 wherein about 0.10 to about 0.15 equivalents of heterocyclic amine catalyst are present.

17. A process in accordance with claim 1 wherein said substantially pure stilbazolium salt is at least about 95% pure.

18. A process in accordance with claim 2 wherein said stilbazolium salt is a substantially pure stilbazolium salt.

19. A process in accordance with claim 18 wherein said substantially pure stilbazolium salt is at least about 95% pure.

* * * * *